United States Patent
Farage

(10) Patent No.: US 9,532,717 B2
(45) Date of Patent: Jan. 3, 2017

(54) METHOD FOR DIAGNOSING VULVOVAGINAL DISORDERS

(75) Inventor: Miranda Aref Farage, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 1801 days.

(21) Appl. No.: 12/259,513

(22) Filed: Oct. 28, 2008

(65) Prior Publication Data

US 2010/0106024 A1    Apr. 29, 2010

(51) Int. Cl.
*A61B 5/00* (2006.01)

(52) U.S. Cl.
CPC ............ *A61B 5/0059* (2013.01); *A61B 5/411* (2013.01); *A61B 5/445* (2013.01)

(58) Field of Classification Search
None
See application file for complete search history.

(56) References Cited

U.S. PATENT DOCUMENTS

| | | | |
|---|---|---|---|
| 4,034,114 A * | 7/1977 | Yu et al. | 514/703 |
| 5,472,964 A * | 12/1995 | Young et al. | 514/243 |
| 5,473,160 A | 12/1995 | Eysel et al. | |
| 5,742,392 A | 4/1998 | Anderson et al. | |
| 6,032,071 A | 2/2000 | Binder | |
| 6,697,156 B1 | 2/2004 | Karp | |
| 6,766,184 B2 * | 7/2004 | Utzinger et al. | 600/407 |
| 6,907,193 B2 | 6/2005 | Kollias et al. | |
| 7,024,037 B2 | 4/2006 | Zhang et al. | |
| 7,167,244 B2 | 1/2007 | Mullani | |
| 7,276,058 B2 | 10/2007 | Altshuler et al. | |
| 7,309,335 B2 | 12/2007 | Altshuler et al. | |
| 7,351,252 B2 | 4/2008 | Altshuler et al. | |
| 2005/0157939 A1 | 7/2005 | Arsenault et al. | |
| 2005/0271598 A1 * | 12/2005 | Friedman et al. | 424/47 |
| 2006/0155194 A1 | 7/2006 | Maracotte et al. | |
| 2006/0264512 A1 * | 11/2006 | Pyke | 514/571 |
| 2007/0237374 A1 | 10/2007 | Nikiforos et al. | |

OTHER PUBLICATIONS

Gale Encyclopeida of Medicine, 3rd ed, 2006 [retrieved on May 23, 2011]. Retrieved from the Internet: <URL: http://www.encyclopedia.com/topic/Vulvovaginitis.aspx>.*
Bergeron et al., Vulvar Vestibulitis Syndrome: Reliability of Diagnosis and Evaluation of Current Diagnostic Criteria, 2001, Obstetrics & Gynecology, 98:1, 45-51.*
"Determining the Cause of Vulvovaginal Symptoms," Miranda A. Farage, PhD, Kenneth W. Miller, PhD, and William J. Ledger, MD, CME Review Article 19, vol. 63, No. 7, Obstetrical and Gynecological Survey, Lippincott Williams & Wilkins. pp. 1-20 pages, 1 pg. Author Queries, Copyright 2008.

(Continued)

*Primary Examiner* — Bo J Peng
(74) *Attorney, Agent, or Firm* — Dara M. Kendall; Roddy M. Bullock; Megan C. Hymore

(57) ABSTRACT

A method for diagnosing the presence of a vulvovaginal disorder is provided. The method uses a source of cross-polarized light to detect subsurface irritation in the vulvovaginal area. The presence of subsurface irritation is then used to diagnose the presence of a vulvovaginal disorder.

11 Claims, 2 Drawing Sheets

(56) References Cited

OTHER PUBLICATIONS

"Enhancement of Visual Scoring of Skin Irritant Reactions Using Cross-Polarized Light and Parallel-Polarized Light," Miranda A. Farage, Contact Dermatitis 2007, Copyright Blackwell Munksguard 2007, pp. 1-9.
"Investigative Study with the Syris V-600 Visualization System vs. Standard Visual Grading", M. A. Farage, PhD, PPCT-04007-MD, Protocol Date: Feb. 13, 2004, pp. 1-17.
"In Vivo Documentation of Cutaneous Imflammation Using Spectral Imaging" G. Stamatas, N. Kollias, Journal of Biomedical Optics 12(5), 051603 (Sep./Oct. 2007), pp. 1-7.
"A Growing Concern: Inability to Diagnose Vulvovaginal Infections Correctly," W. J. Ledger, MD and G. R. G. Monif, MD, Copyright American College of Obstetricians and Gynecologists, vol. 103, No. 4, Apr. 2004, pp. 782-784.
"In Vivo Monitoring of Cutaneous Edema Using Spectral Imaging in the Visible and Near Infrared," G. N. Stamatas, M. Southall, and N. Kollias, Journal of Investigative Dermatology (2006) 126, 1753-1760. pp. 1-10.
Mackinnon, N.B. et al., "Design of a multispectral digital colposcope" Progress in Biomedical Optics and Imaging—Proceedings of Spie—Advanced Biomedical and Clinical Diagnostic Systems, V. 2007 Spie US, vol. 6430, 2007, XP 002564714.
U.S. Appl. No. 11/715,625, filed Mar. 8, 2007, Miranda Aref Farage.

\* cited by examiner

METHOD FOR DIAGNOSING VULVOVAGINAL DISORDERS

FIELD OF THE INVENTION

The present invention relates to methods using cross-polarized light to diagnose the presence of vulvovaginal disorders.

BACKGROUND OF THE INVENTION

There are several disorders that affect the vulvovaginal area, examples of which include vulvodynia and vulvar vestibulitis syndrome. These diseases can case discomfort, and in some instances if left untreated can lead to more severe ailments. Due to the physical location of the diseases they are often difficult to diagnose, as visual assessments of vulvovaginal irritation can be quite difficult. Genital pigmentation and blood flow create an erythematous appearance that can mask underlying epithelial irritation. Moreover, certain vulvovaginal syndromes, such as vulvar vestibulitis syndrome and idiopathic vulvodynia, cause perplexing sensory effects without objective visual findings. Adding to the complication of proper diagnosis is that often the discomfort associated with the disease has no corresponding physical symptoms. This leads practitioners to inaccurate or incorrect diagnosis.

Presently most practitioners use some form of visual assessment of the vulvovaginal skin surface area to diagnose the cause of any discomfort. Such visual assessment is usually done with a colposcope. A colposcope functions as a lighted binocular microscope to magnify the skin surface view of the vulvovaginal area. However, when using visual assessment, discomfort in the vulvovaginal area is not always correlated with detectable physical symptoms. Thus, the absence of skin or mucosal lesions or visual signs of irritation cannot be explained and sometimes cannot be clear.

It would be desirable to provide a method that detects subsurface irritation indicative of vulvovaginal disorders.

SUMMARY OF THE INVENTION

A method of diagnosing the presence of a vulvovaginal disorder is provided. The method comprises the steps of providing a source of cross-polarized light; illuminating an anatomical site of the vulvovaginal area; viewing the cross-polarized light to detect presence of subsurface irritation at the anatomical site; and diagnosing existence of vulvovaginal disorder.

A method of determining effectiveness of treating a vulvovaginal disorder is provided. The method comprises the steps of providing a source of cross-polarized light; illuminating an anatomical site of the vulvovaginal area; viewing the cross-polarized light to detect presence of subsurface irritation at the anatomical site; making a first recording of the severity of subsurface irritation and diagnosing existence of a vulvovaginal disorder; treating the vulvovaginal disorder; providing a source of cross-polarized light; illuminating the anatomical site of the vulvovaginal area; viewing the cross-polarized light to detect presence of subsurface irritation at the anatomical site; making a second recording of the severity of subsurface irritation; and comparing the first recording of the severity of subsurface irritation with the second recording of the severity of subsurface irritation.

DETAILED DESCRIPTION OF THE INVENTION

Figure 1:
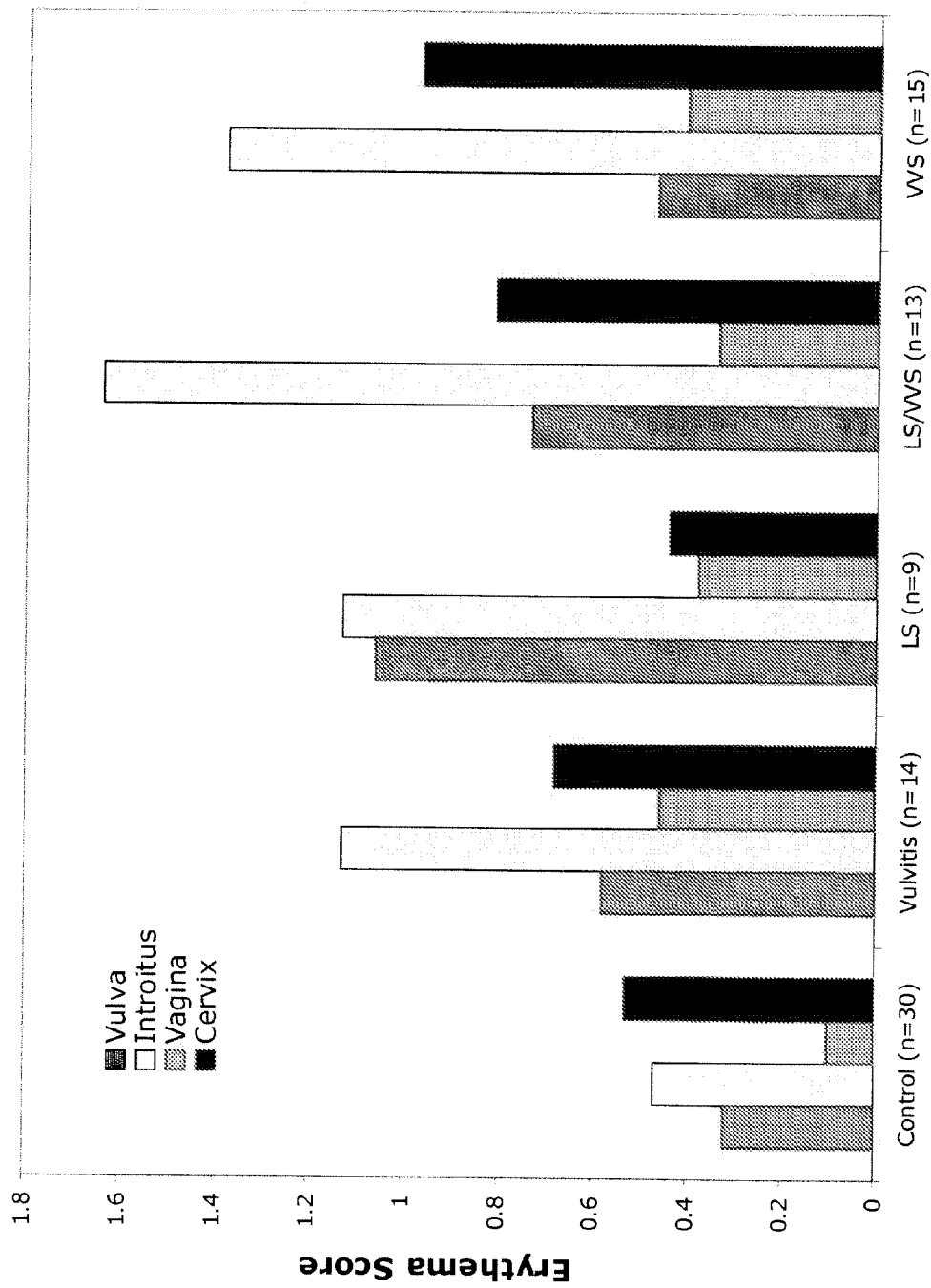
FIG. 1 is a graph showing levels of erythema.

The present invention comprises a method for diagnosing the presence of vulvovaginal disorders. The method uses cross-polarized light to detect subsurface irritation, which may be an indicator of a vulvovaginal disorder. A medical practitioner can evaluate the subsurface irritation, in certain embodiments in combination with an individual's self reported discomfort in the vulvovaginal area, to diagnose the presence of one or more vulvovaginal disorders.

The term "vulvovaginal" encompasses the pudendal region of a human female, and includes anatomical sites such as the vulva, introitus, vagina, and cervix.

The term "subsurface irritation", as used herein, refers to irritation of the epithelial subsurface of an anatomical site of the vulvovaginal area, wherein the irritation may be erythema, inflammation, or dryness.

The term "erythema", as used herein, refers to redness of the skin.

The term "dryness", as used herein, refers to powderiness or cracking of the skin.

The term "inflammation", as used herein, refers to a local response to cellular injury that is marked by capillary dilatation.

The term "vulvovaginal disorder," as used herein, refers to both common and uncommon conditions associated with vulvovaginitis, including vulvitis, vulvar vestibulitis syndrome, Lichen sclerosus, allergic contact dermatitis, systemic dermatoses, rare autoimmune diseases, and neuropathic vulvar pain syndromes and sensory symptoms (itch or pain, localized or generalized, provoked, intermittent or chronic).

The present invention is a reliable method for diagnosing the presence of one or more vulvovaginal disorders. The method uses polarized light, and a polarized viewer to produce cross-polarized light to detect subsurface irritation such as erythema, inflammation, or dryness. The presence of subsurface irritation in the vulvovaginal area can then be used to diagnose a vulvovaginal disorder. The diagnosis may be based on factors such as the location of the subsurface irritation in the vulvovaginal area (vulva, introitus, vagina, and cervix); the type of subsurface irritation, such as erythema, inflammation, or dryness; or the severity of the subsurface irritation, which would include the size and depth of the subsurface irritation.

When light encounters the skin surface, about five percent (5%) is reflected. This reflected light only carries information about the shape and texture of the skin surface. The remaining 95% of light enters the skin, where it encounters structures that either scatter or absorb the light. Some of the light that is scattered exits out of the skin. This back-scattered light component carries information about subsurface skin structures such as blood vessels, pigmentation, hair follicles, skin color, inflammation, and erythema. Back scattering scrambles polarization, which is the orientation of light waves, whereas light reflected from the skin surface does not. Therefore, an instrument such as the v600, produced by Syris Scientific LLC of Gray, Me., that uses a polarized illuminating light, combined with polarized viewing, separates the two components (specular reflection/back scattering) of skin reflectance. By crossing the polarizing illuminating light and viewing polarizers to produce a source of cross-polarized light, the reflected component is blocked, providing a greatly enhanced view below the skin surface (subsurface).

The method of the present invention may also be used to monitor the treatment of vulvovaginal disorders. For example, after using cross-polarized light to diagnose a vulvovaginal disorder the individual having the vulvovaginal disorder may receive treatment, such as the administration of antibiotics or the application of topical treatments to the affected anatomical site or sites. The use of cross-polarized light could then be used to compare the present level of subsurface irritation in the affected anatomical site with the level of subsurface irritation at the site when a diagnosis of a vulvovaginal disorder was made. The result of the comparison of subsurface irritation levels could then be used to prescribe need for or form of continuing treatment.

EXAMPLES

Eighty-one (81) female test participants between the ages of 19-75, with very sensitive to moderately sensitive skin (Types I-IV), as determined by Fitzpatrick's classifications, as disclosed in The Validity And Practicality Of Sun-Reactive Skin Types I Through VI Archives Dermatology 1988 June; 124(6):869-71., participated in the study. For each participant a medical and gynecological history, including details of menstrual, contraceptive, and parturition history and frequency of genital infections in the previous twelve (12) months, was obtained. Each participant also under went a physical examination in a clinical setting to determine the presence or absence of symptoms for a vulvovaginal disorder.

Based on the medical history, gynecological history, and presence or absence of symptoms for a vulvovaginal disorder (symptoms) participants were placed in either a symptoms group (for a vulvovaginal disorder) or a control group. Participants diagnosed as having symptoms upon physical examination of the vulvovaginal area and having a history of such symptoms were assigned to the symptoms group. Participants having no history of symptoms for at least six (6) months and absence of symptoms upon physical examination were assigned to the control group. Fifty-one (51) participants were allocated to the symptoms group and thirty (30) were allocated to the control group.

The symptoms group was divided into four (4) subgroups based upon medical history, gynecological history, and physical examination: fourteen (14) in a vulvitis subgroup; fifteen (15) in a vulvar vestibulitis syndrome (VVS) subgroup; nine (9) in a Lichen sclerosus subgroup (LS); and thirteen (13) in a vestibulitis syndrome/Lichen sclerosus subgroup (VVS/LS). The control group was made up of participants with no symptoms and no abnormal findings.

This study compared three evaluation techniques (unaided visual examination, colposcopy, and cross-polarized light) for their relative sensitivities in detecting vulvovaginal erythema and dryness in both the control group and symptoms group. This was done by examining the vulvovaginal areas comprising the anatomical sites including the vulva, introitus, vagina, and cervix.

Standard scoring scales for erythema and dryness were used. Erythema was scored on a 5-point scale, where 0=no apparent cutaneous changes; 1=faint but definite erythema, no eruptions or broken tissue, or no erythema but definite dryness; 2=moderate erythema, may have had papules or fissures, moderate to severe erythema in the cracks; 3=severe erythema (beet redness), may have had generalized papules, or moderate to severe erythema with slight edema; 4=generalized vesicles or eschar formation or spreading moderate-to-severe erythema. Half integers could be assigned.

TABLE 1

Erythema Scoring Scale

| | |
|---|---|
| 0 | No apparent cutaneous involvement |
| 0.5 | Faint, barely perceptible erythema |
| 1 | Faint, but definite erythema |
| 1.5 | Well-defined erythema |
| 2 | Moderate erythema; may have papules or deep fissures |
| 2.5 | Moderate erythema with barely perceptible edema; may have a few papules |
| 3 | Severe erythema (beet redness); may have generalized papules |
| 3.5 | Moderate-to-severe erythema with moderate edema |
| 4 | Moderate-to-severe erythema and/or extending edema, may have generalized vesicles or eschar formations |

Dryness was scored on a 7-point scale, where 0=none; 1=patches of cracking and/or slight powderiness, and occasional patches of small scale; 2=generalized, slight powderiness; cracking and occasional lifting scales may be present; 3=generalized, moderate powderiness and/or moderate cracking and scales; 4=generalized, heavy powderiness and/or heavy cracking and lifting scales; 5=generalized, high cracking and lifting scales; eczematous change may have been present but not prominent; may have observed bleeding cracks; 6=generalized, severe cracking; bleeding cracks and eczematous changes may have been present, and large scales may have been sloughing.

At each anatomical site (vulva, introitus, vagina, and cervix) three (3) evaluation techniques were performed sequentially to evaluate erythema and dryness: (i) unaided visual scoring; (ii) colposcopy; and (iii) enhanced visualization with cross-polarized light (epithelial subsurface evaluation). After scoring with each technique, the apparent diagnosis was also recorded, if applicable.

As shown in Table 2, the use of cross-polarized light for subsurface visualization was significantly more sensitive than either unaided visual examination or colposcopy for discerning erythema and dryness.

| | Erythema Scores | | | |
|---|---|---|---|---|
| | Vulva | Introitus | Vagina | Cervix |
| Symptoms Group | | | | |
| Unaided visual examination | 0.18 | 0.59 | 0.11 | 0.38 |
| Colposcopy | 0.19 | 0.59 | 0.12 | 0.38 |
| Cross-polarized light* | 0.64 | 1.33 | 0.42 | 0.81 |
| Control Group | | | | |
| Unaided visual examination | 0.02 | 0.17 | 0.03 | 0.25 |
| Colposcopy | 0.02 | 0.17 | 0.03 | 0.27 |
| Cross-polarized light* | 0.32 | 0.47 | 0.01 | 0.53 |

As shown in Table 2, using cross-polarized light, erythema was visualized with greater sensitivity than either unaided visual examination or colposcopy at all anatomical sites (vulva, introitus, vagina, and cervix) within both the control and symptomatic groups. By contrast unaided visual examination and colposcopy did not differ in their sensitivity for assessing erythema within each group.

As shown in Table 3, the use of cross-polarized light for subsurface visualization was also significantly more sensitive than unaided visual examination and colposcopy for discerning dryness, specifically on the vulva in controls and on the vulva and introitus in symptomatic participants. Negligible dryness was observed at other sites in either group.

| Dryness scores | | | | |
|---|---|---|---|---|
| | Vulva | Introitus | Vagina | Cervix |
| Symptoms Group | | | | |
| Unaided visual examination | 0.52 | 0.15 | 0.02 | 0.02 |
| Colposcopy | 0.52 | 0.15 | 0.02 | 0.02 |
| Cross-polarized light* | 1.26 | 0.31 | 0.02 | 0.02 |
| Control Group | | | | |
| Unaided visual examination | 0.43 | 0.03 | 0.0 | 0.0 |
| Colposcopy | 0.40 | 0.03 | 0.0 | 0.0 |
| Cross-polarized light* | 0.97 | 0.07 | 0.0 | 0.0 |

*using Syris v600 ™

All techniques detected significantly elevated erythema on the vulva and the introitus of symptomatic participants. However, only the use of cross-polarized light revealed increased erythema in the vagina (Table 2) and elevated dryness on the vulva and introitus of symptomatic participants relative to controls (Table 3). No differences in cervical erythema were found between participants and controls using any technique. Vaginal or cervical dryness were negligible in both groups.

Figure 2:
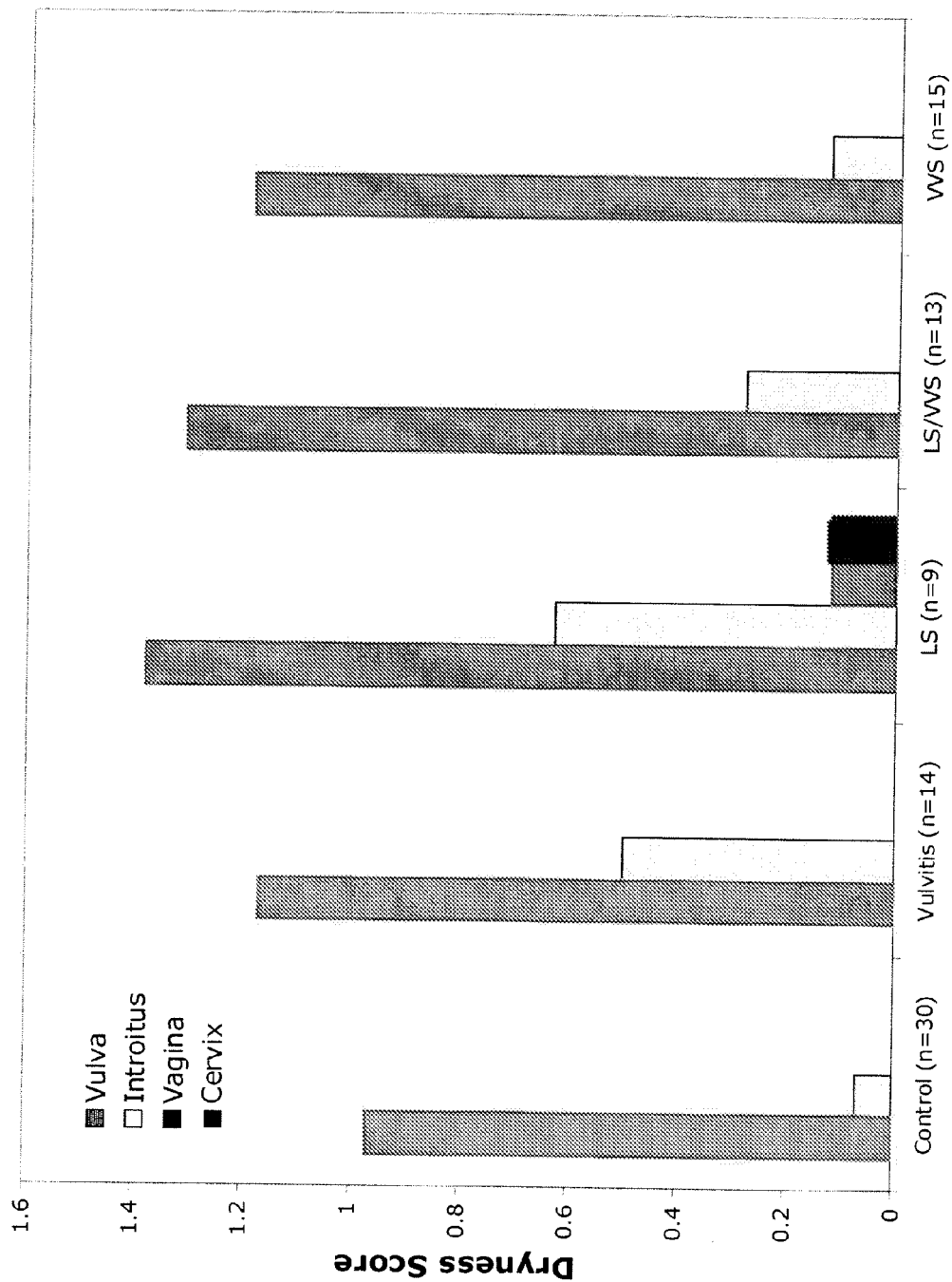
FIG. 2 is a graph showing levels of dryness.

FIG. 1 shows levels of erythema detected at anatomical sites (vulva, introitus, vagina, and cervix) for the control group and symptomatic subgroups using the Syris v600™ (cross-polarized light). As shown in FIG. 1 however, in symptomatic subgroups of participants (vulvitis, LS, LS/VVS, and VVS), only the use of cross-polarized light detected elevated erythema at other sites (vulva, vagina and cervix). The use of cross-polarized light demonstrated erythema was significantly elevated on the vulva in the LS and LS/VVS subgroups; on the vagina in the vulvitis, LS/VVS, and VVS subgroups; and on the cervix in the VVS subgroup only. FIG. 2 shows levels of dryness detected at anatomical sites (vulva, introitus, vagina, and cervix) for the control group and symptomatic subgroups using the Syris v600™ (cross-polarized light). As shown in FIG. 2, elevated dryness relative to the control group was observed on the vulva of the LS/VVS subgroup and the LS subgroup and on the introitus of the vulvitis subgroup and the LS subgroup.

An interesting finding was that although the vulva of VVS participants appeared clinically normal with all visualization techniques, cross-polarized light revealed in VVS participants an increase in erythema relative to the control group at all other anatomical sites (introitus, vagina and cervix). Moreover, the VVS subgroup was the only group in this study in which elevated subsurface erythema was observed concurrently on the introitus, vagina, and cervix, as shown in FIG. 1.

Interestingly, the use of cross-polarized light, but not other methods detected elevated vaginal erythema in certain symptomatic subgroups (vulvitis, LS/VVS and VVS) clinically characterized primarily by their vulvar signs and symptoms. The participants of the LS symptomatic subgroup did not exhibit erythema or dryness of the subsurface of the vagina.

The results of the study showed that the use of cross-polarized light was more sensitive in detecting erythema than unaided visual examination or colposcopy, regardless of whether or not the participants had symptoms of one or more vulvovaginal disorders (vulvitis, LS, LS/VVS, and VVS). Visualization of the subsurface of the epithelium using cross-polarized light was more revealing of erythematous changes in the vulvovaginal area than either unaided visual examination or colposcopy. Moreover, although all visualization techniques detected heightened vulvar erythema among the symptoms group relative to the control group, the use of cross-polarized light was the only method that revealed elevated vaginal erythema among the symptoms group generally and in specific symptomatic subgroups (vulvitis, LS/VVS, and VVS). The use of cross-polarized light was also more sensitive in detecting changes in dryness of the vulva and introitus. The vagina and cervix, which are moist tissues, exhibited no significant dryness with any method. Further, although the vulva of participants in the symptomatic group diagnosed with VVS appeared normal with all techniques only the use of cross-polarized light detected erythema of the epithelial subsurface. Therefore, the use of cross polarized light detected the presence of elevated subsurface erythema concurrently on the introitus, vagina, and cervix of VVS participants despite a normal clinical appearance of the labia.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An enhanced and improved method of diagnosing the subsurface presence of vulvovaginitis comprising:
   a. providing a source of cross-polarized light;
   b. illuminating an anatomical site of the vulvovaginal area with the cross-polarized light in vitro or in vivo;
   c. viewing the cross-polarized light to detect presence of subsurface irritation at the anatomical site; and
   d. diagnosing the presence of vulvovaginitis;
   wherein the anatomical site is at least one of the vulva, introitus, or vagina;
   wherein the subsurface irritation is at least one of erythema or dryness; and
   wherein the vulvovaginitis includes at least one of vulvar vestibulitis syndrome, or Lichen sclerosus.

2. The method of claim 1 wherein an instrument provides the source of cross-polarized light.

3. The method of claim 2 wherein the instrument blocks a reflected component, thus providing a greatly enhanced view of subsurface irritation at the anatomical site.

4. A method for monitoring the treatment of subsurface vulvovaginitis comprising:

a. providing a source of cross-polarized light;
b. illuminating an anatomical site of the vulvovaginal area with the cross-polarized light in vitro or in vivo;
c. viewing the cross-polarized light to detect presence of subsurface irritation at the anatomical site;
d. diagnosing the presence of vulvovaginitis;
e. treating the vulvovaginitis;
f. providing the source of cross-polarized light;
g. illuminating the anatomical site of the vulvovaginal area with the cross-polarized light in vitro or in vivo;
h. viewing the cross-polarized light to detect the presence of subsurface irritation at the anatomical site; and
i. comparing the subsurface irritation prior to treating the vulvovaginitis with the subsurface irritation after treating the vulvovaginitis;
wherein the anatomical site is at least one of the vulva, introitus, or vagina; and
wherein the subsurface irritation is at least one of erythema or dryness.

5. The method of claim 4 wherein the vulvovaginitis includes at least one of vulvitis, vulvar vestibulitis syndrome, or Lichen sclerosus.

6. The method of claim 4 wherein the treating is at least one of administering antibiotics or application of a topical agent.

7. The method of claim 4 wherein an instrument provides the source of cross-polarized light.

8. The method of claim 7 wherein the instrument blocks a reflected component, thus providing a greatly enhanced view of subsurface irritation at the anatomical site.

9. A method for monitoring the treatment of subsurface vulvar vestibulitis syndrome comprising:
a. providing a source of cross-polarized light;
b. illuminating an anatomical site of the vulvovaginal area with the cross-polarized light in vitro or in vivo;
c. viewing the cross-polarized light to detect presence of subsurface irritation at the anatomical site;
d. diagnosing the presence of vulvar vestibulitis syndrome;
e. treating the vulvar vestibulitis syndrome;
f. providing the source of cross-polarized light;
g. illuminating the anatomical site of the vulvovaginal area with the cross-polarized light in vitro or in vivo;
h. viewing the cross-polarized light to detect the presence of subsurface irritation at the anatomical site; and
i. comparing the subsurface irritation prior to treating the vulvar vestibulitis syndrome with the subsurface irritation after treating the vulvar vestibulitis syndrome;
wherein the anatomical site is at least one of the vulva, introitus, or vagina; and
wherein the subsurface irritation is at least one of erythema or dryness.

10. The method of claim 9 wherein the treating is at least one of administering antibiotics or application of a topical agent.

11. The method of claim 9 wherein an instrument provides the source of cross-polarized light, and wherein the instrument blocks a reflected component, thus providing a greatly enhanced view of subsurface irritation at the anatomical site.

* * * * *